United States Patent [19]

Hirai et al.

[11] Patent Number: 4,832,488
[45] Date of Patent: May 23, 1989

[54] METHOD FOR CORRECTION OF CALIBRATION CURVE IN DRY ANALYTICAL PROCESS

[75] Inventors: Kikuo Hirai; Fuminori Arai; Yuzo Iwata, all of Asaka, Japan

[73] Assignee: Fuji Photo Film Co., Ltd., Kanagawa, Japan

[21] Appl. No.: 91,886

[22] Filed: Sep. 1, 1987

[30] Foreign Application Priority Data

Sep. 1, 1986 [JP] Japan ................................ 61-205345

[51] Int. Cl.$^4$ .................. G01J 3/50; G01N 21/49; G01N 33/48
[52] U.S. Cl. .................................. 356/243; 356/402; 356/446
[58] Field of Search .................. 356/243, 446, 402

[56] References Cited

U.S. PATENT DOCUMENTS 3,907,503 9/1975 Betts et al. .......................... 356/446
4,509,859 4/1985 Markart et al. ..................... 356/243

Primary Examiner—Vincent P. McGraw
Attorney, Agent, or Firm—Jules E. Goldberg

[57] ABSTRACT

A method for correction of calibration curve in a dry analytical process for quantitative analysis of analyte in a liquid sample such as blood is disclosed. In the method, a calibration curve which has been previously determined for analysis of the analyte using a standard dry analytical element is corrected for application to a dry analytical element having deviated from the standard dry analytical element in its sensitivity to the analyte due to unintentional denaturation, variation, etc., utilizing an optical density determined on the above deviated dry analytical element which has not received spotting of a liquid sample containing the analyte.

4 Claims, 2 Drawing Sheets

FIG. I

METHOD FOR CORRECTION OF CALIBRATION CURVE IN DRY ANALYTICAL PROCESS

BACKGROUND OF THE INVENTION

1. Field of the Invention

This invention relates to a method for correction of calibration curve in dry analytical processes which are performed for quantitative analysis of a specific component (analyte) in various fluids, typically blood.

2. Description of Prior Art

In performing an analytical process using a dry analytical element (i.e., analytical element for dry chemistry), a calibration curve showing a relationship between content or concentration of an analyte and optical denisty measured thereon is initially prepared, using a plurality of liquid samples containing the analyte in known different concentration. A concentration (this representing concentration as well as content) of the analyte in a test samppple is then determined utilizing the above-prepared calibration curve.

Generally, a calibration curve for a dry analytical element is composed of not a simple straight line but a curved line within whole measurable concentration range. Therefore, a calibration curve for the use in an precise analysis is generally prepared by graphically connecting at least three analytical data in sequence which have been determined on at least three samples having a known concentration.

It is known that characteristics of a dry analytical element slightly vary depending upon denaturation of reagents in the element in the course of storage, variation of temperature for measurement, variation of conditions for the preparation of the element, etc. This means that optical density values measured on the same liquid sample using analytical elements prepared in accordance with the same specification may fluctuate. The relationship between concentrations of the analyte and optical density values therefor can be represented by Curve B (shifted calibration curve) of FIG. 1, which is diferrent (or shifted) from Curve A (standard calibration curve). In this case, an optical density value measured on a certain liquid sample using a dry analytical element showing the shifted calibration curve is shifted from an optical density value which is ought to be given if a standard analytical element used for the preparation of the standard calibration curve is employed. In this case, if the shifted value or the variation of the calibration curve is determined in advance of or just prior to the analytical operation using the denatured (or modified, etc) analytical element, the corrected concentration of analyte is given through correcting the shifted calibration curve to accord with the standard calibration curve.

In the heretofore known method for correction of calibration curve, one or more reference liquids (i.e., liquid samples containing the analyte of a known concentration) are used for estimation of shifted optical density value, and the estimated shifted value is then subjected to calculation according to a predetermined equation for correcting the calibration curve.

In the above method, it is necessary that at least one reference liquid containing the analyte of known concentration is used. It is further necessary that at least one analytical element is used only for the procedure for the correction of calibration curve, because a dry analytical element having been used for the correction per se can be no more employed for actual analysis.

Further, the above known method for correction of calibration curve requires not only a period of time for spotting the reference liquid on a test analytical element and then photometrically determining an optical density value after incubation, but also a period of time for precisely determining the concentration of analyte in the reference liquid using another standard measuring method.

Furthermore, it is possible that the reference liquid containing the analyte of known conentration vary in its concentration of the analyte in the course of storage or due to contamination with other components. In this case, the correction of calibration curve is not precisely made.

As is described hereinbefore, a calibration curve for a dry analytical element generally is in the form of a curve, even though it contains a portion of seemingly straight line. Accordingly, it has been considered that precise correction of calibration curve requires numerical correction using a combination of a linear equation, a quadratic equation, a cubic equation, and equations of higher degree.

SUMMARY OF THE INVENTION

It has been now surprisingly discovered by the present inventors that the precise correction of calibration curve can be accomplished by processing an optical density value measured on an analytical element without spotting a reference liquid or an analytical element with spotting a liquid containing no analyte using a correcting equation comprising a specific linear or quadratic equation.

Accordingly, it is an object of the present invention to provide a method for correction of calibration curve for a dry analytical element which is assumed as having slightly varied in its sensitivity due to denaturation of reagents in the element in the course of prolonged storage by elevation of surrounding temperature, etc, or due to modification (or variation) of conditions for the preparation of the element, etc.

It is another object of the invention to provide a method for correction of shifted calibration curve of the above-mentioned denatured or modified analytical element with practically sufficient high precision employing no reference liquid (i.e., aqueous liquid sample containing analyte of known concentration).

There is provided by the present invention a method for correction of a calibration curve in a dry analytical process for quantitative analysis of an analyte in a liquid sample, wherein a calibration curve which has been previously determined for analysis of the analyte using a standard dry analytical element is corrected for application to a dry analytical element having deviated from the standard dry analytical element in its sensitivity to the analyte, utilizing an optical density value determined on the deviated dry analytical element which has not received application of a liquid sample containing the analyte.

According to the method of the present invention, the correction of a shifted calibration curve can be accomplished simply by measuring an optical density ($F_D^*$) of an analytical element (which varies, or which is assumed to vary, in its sensitivity) without spotting a reference liquid on the analytical element.

DETAILED DESCRIPTION OF THE INVENTION

Figure 1:
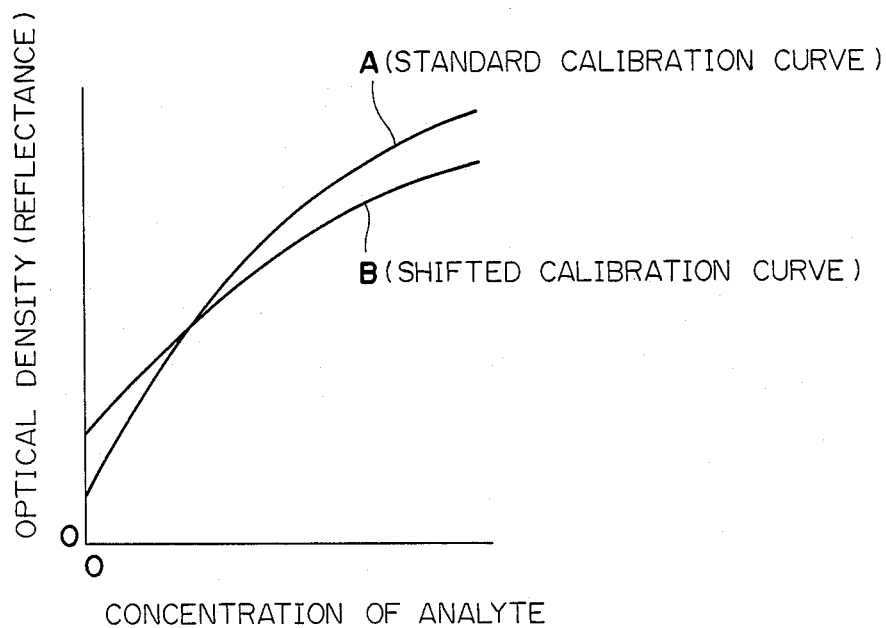
FIG. 1 schematically shows a relationship between a standard (normal) calibration curve A and a shifted calibration curve B.

In the analytical operation using a dry analytical element, one or more drops of a liquid sample containing analyte of unknown concentration are first deposited (hereinafter referred to as "spotting") on a uppor surface of the element or on a surface of a spreading layer arranged on the analytical element. The analytical element is then incubated at a given temperature for a given period of time for accomplishing color-formation or color-change in the element. The color is then photometrically measured, and the measured value is converted into a concentration of the analyte using a predetermined calibration curve. The calibration curve is prepared using a relationship between concentration of analyte (C) and measured optical density value ($D_S$) via a function (f), which is given as follows:

$$C = f(D_S) \quad (1)$$

The calibration curve can be expressed in a graph or in a table.

As described previously, a standard analytical element and a denatured or modified analytical element probably give optical density values which are different from each other when a liquid sample containing analyte of the same concentration is spotted. Moreover, the standard analytical element and the denatured or modified analytical element probably give optical density values which are different from each other, when a liquid sample is not spotted and on incubation is performed, when a liquid sample is spotted and incubation is performed, or when a pure water of a liquid containing no analyte such as control serum or physiological saline solution is spotted and incubation is performed.

According to study of the present inventors, it has been discovered that there is a certain relationship among the degrees of difference of the optical density value measured in these differnet phases for a standard analytical element and a denatured or modified analytical element. The relationship can be described in the following manner:

$$D_{S1} - D_{S1}^* = G_1(F_{D1} - F_{D1}^*) \quad (2)$$

$$D_{S2} - D_{S2}^* = G_2(F_{D2} - F_{D2}^*) \quad (3)$$

In the above equations, $D_{S1}$ and $D_{S2}$ respectively mean optical density values measured for two liquid samples or two reference liquids containing analyte of known but different concentrations, using a standard (i.e, normal) dry analytical element and performing normal analytical operations (which comprises) spotting a liquid sample on a dry analytical element, incubating the element, and then measuring color developed on the element by reflection photometry);

$D_{S1}^*$ and $D_{S2}^*$ respectively mean optical density values measured for two same liquid samples or reference liquids as above, using a denatured (or modified due to variation of conditions of preparation of an analytical element) dry analytical element and performing the normal analytical operations;

$F_{D1}$ and $F_{D2}$ respectively mean optical density values measured on the normal dry analytical element having been spotted with no liquid sample and not subjected to incubation, the normal dry analytical element having been spotted with no liquid sample but subjected to incubation, or the normal dry analytical element having been spotted with a liquid sample but not subjecteed to incubation; and $F_{D1}^*$ and $F_{D2}^*$ respectively mean optical density values measured on the denatured or modified dry analytical element having been spotted with no liquid sample and not subjected to incubation, the denatured or modified dry analytical element having been spotted with no liquid sample but subjected to incubation, or the denatured or modified dry analytical element having been spotted with a liquid sample but not subjecteed to incubation.

The above-described relationship can be represented by the following general equation:

$$D_S - D_S^* = G(F_D - F_D^*) \quad (4)$$

As described above, there is a certain relationship between difference between $G_1$ and $G_2$ and difference between $D_{S1}$ and $D_{S2}$, which can be expressed by the following equation:

$$G_1 - G_2 = a(D_{S1} - D_{S2}) \quad (5)$$

(in the equation, "a" is a constant).

The equation (5) can be converted through integration into the following general equation:

$$G = aD_S + b \quad (6)$$

(in the equation, "b" is another constant).

The equations (4) and (6) are combined to give the following equation:

$$D_S - D_S^* = (aD_S + b) \cdot (F_D - F_D^*) \quad (7)$$

The equations (1) and (7) are combined to give the following equation:

$$C = f((aD_S + b) \cdot (F_D - F_D^*) + D_S^*) \quad (8)$$

Therefore, if $F_D$ is previously known, the following can be done:

(1) a shifted calibration curve for a denatured or modified analytical element can be obtained by simply measuring an optical density (of color) of the denatured or modified element and correcting a standard calibration curve using the measured optical density;

(2) a shifted calibration curve for a denatured or modified analytical element can be obtained by measuring an optical density of the denatured or modified element after it is simply incubated with no spotting of a liquid sample, and then correcting a standard calibration curve using the measured optical density;

(3) a shifted calibration curve for a denatured or modified analytical element can be obtained by measuring an optical density of the denatured or modified element after it is spotted with water (e.g., pure water) or an aqueous liquid containing no analyte (e.g., control serum or phosiological saline solution) and no incubation is performed, and correcting a standard calibration curve using the measured optical density; and (4) a shifted calibration curve for a denatured or modified analytical element can be obtained by measuring an optical density of the denatured or modified element after it is spotted with water or the aqueous liquid containing no analyte and then incubated, and then correcting a standard calibration curve using the measured optical density.

A shifted calibration curve can be also converted into a standard calibration curve in the above manner.

In any of the above procedures, satisfactorilly precise correction of the standard calibration curve into a shited calibration curve or vice versa can be accomplished.

The correction method of the present invention can be applied to analytical processes using the following dry analytical elements: an integral multilayer analytical element having a spreading layer of woven fabric described, for example, in Japanese Patent Provisional Publications No. 55(1980)-164356 and No. 57(1982)-66359; an integral multilayer analytical element having a spreading layer of knitted fabric described, for example, in Japanese Patent Provisional Publication No. 60(1985)-222769; an integral multilayer analytical element having a spreading layer of paper containing an organic polymer fiber pulp described, for example, in Japanese Patent Provisional Publication No. 57(1982)-148250; an integral multilayer analytical element having a porous layer combined via porous (partial) adhesion described, for example, in Japanese Patent Provisional Publication No. 61(1986)-4959; an integral multilayer analytical element having a fibrous spreading layer which has been prepared by coating a fiber dispersion stated, for example, in Japanese Patent Provisional Publication No. 57(1982)-125847; an integral multilayer analytical element having a nonfibrous isotropic porous spreading layer such as a membrane filter (blushed polymer layer) or a continuous void-containing porous layer comprising polymer microbeads dispersed in a hydrophilic polymer binder stated, for example, in Japanese Patent Publication No. 53(1978)-21677 and U.S. Pat. No. 3,992,158; an integral multilayer analytical element having a nonfibrous isotropic porous spreading layer of a continuous void-containing porous layer (three-dimensional lattice matrix composed of granules) comprising polymer microbeads bound to each other with point-to-point contact by a water-unswellable polymer adhesive and other similar integral multilayer analytical elements described, for example, in Japanese Patent Provisional Publication No. 55(1980)-90859; a multilayer analytical element having a fixed laminate of a porous layer described, for example, in Japanese Patent Provisional Publication No. 49(1974)-11395; a multilayer analytical element for immunoassay having a fibrous porous layer described, for example, in Japanese Patent Provisional Publication No. 59(1984)-77356; and an analytical element of improved stick type described, for example, in Japanese Patent Provisional Publications No. 57(1982)-5361 and No. 58(1983)-45565. The correction method of the present invention is particularly advantageously applied to an analytical process using an integral multilayer analytical element.

The following examples are provided to illustrate the present invention in more detail.

REFERENCE EXAMPLE 1

On a colorless, transparent polyethylene terephthalate (PET) film (thickness 185 μm, serving as support) having a gelatin undercoating was coated a color-forming layer of a color-forming reagent composition for glucose measurement. The color-forming layer was prepared by coating an aqueous solution of the reagent composition on the support in such an amount that each component of the reagent compositon was coated in the amount described below and then drying the coated layer.

| Color-Forming Reagent Composition (Coated Amount) | |
|---|---|
| Peroxidase | 5,000 IU/m$^2$ |
| 1,7-Dihydroxynaphthalene | 250 mg/m$^2$ |
| 4-Amino-2,3-dimethyl-1-(2,4,6-trichlorophenyl)-3-pyrazolin-5-one | 1.8 g/m$^2$ |
| Gelatin | 20 g/m$^2$ |
| Nonylphenoxypolyethoxyethanol (containing 10 (average) oxyethylene units) | 200 mg/m$^2$ |

On the color-forming layer was provided a glucose oxidase-containing light-blocking layer. The light-blocking layer was prepared by coating an aqueous solution of the following composition on the color-forming layer in such an amount the each component was coated in the amount described below and then drying the coated layer.

| Light-Blocking Layer Composition (Coated Amount) | |
|---|---|
| Glucose Oxidase | 4,000 IU/m$^2$ |
| Nonylphenoxypolyethoxyethanol (containing 10 (average) oxyethylene units) | 200 mg/m$^2$ |
| Titanate dioxide Fine Particles | 40 g/m$^2$ |

On the glucose oxidase-containing light-blocking layer was provided an adhesive layer by coating an aqueous solution of the following composition on the light-blocking layer in such an amount that each component was coated in the amount described below and then drying the coated layer.

| Adhesive Layer Composition (Coated Amount) | |
|---|---|
| Gelatin | 6.7 g/m$^2$ |
| Nonylphenoxypolyethoxyetanol (containing 10 (average) oxyethylene units) | 200 mg/m$^2$ |

On the adhesive layer was supplied water in an amount of 30 g/m$^2$ to wet the adhesive layer and then pressed lightly a broad cloth (cotton 100%) for lamination. The broad cloth was dried to give a porous spreading layer. Thus, an integral multilayer analytical element for quantitative analysis of glucose was prepared.

The multilayer analytical element was cut into square chips (15 mm × 15 mm), which were then encased in plastic mounts described in Japanese Patent Provisional Publication No. 57(1972)-62452 to obtain analytical slides for glucose determination.

EXAMPLE 1

The following six liquid samples containing glucose of known amount were prepared. The glucose concentration was determined according to Hexakinase-G-6-PHD method.

| Sample 11: | |
| --- | --- |
| Human serum albumin | 700 mg |
| Sodium chloride | 90 mg |
| Add water to make | 10 ml |
| (Glucose concentration: 0 mg/dl) | |
| Sample 12: | |
| Monitrol IX (avaliable from American Dade Corp.) | |
| (Glucose concentration: 90 mg/dl) | |
| Sample 13: | |
| Monitrol IIX (avaliable from American Dade Corp.) | |
| (Glucose concentration: 229 mg/dl) | |
| Sample 14: | |
| Monitrol IX to which glucose was added and dissolved | |
| (Glucose concentration: 493 mg/dl) | |
| Sample 15: | |
| Human serum albumin | 700 mg |
| Sodium chloride | 90 mg |
| Glucose | 10 mg |
| Add water to make | 10 ml |
| (Glucose concentration: 100 mg/dl) | |
| Sample 16: | |
| Human serum albumin | 700 mg |
| Sodium chloride | 90 mg |
| Glucose | 30 mg |
| Add water to make | 10 ml |
| (Glucose concentration: 300 mg/dl) | |

A plurality of analytical slides prepared in the manner as described in Reference Example 1 were divided into three groups, which were denatured by keeping them, respectively, under conditions of a surrounding temperature of 35° C. and a relative humidity of 30% for 3 months, 7 months and 12 months.

The above denatured slides and a freshly prepared analytical slide (which was prepared in the same manner as described in Reference Example 1, for the preparation of a standard calibration curve) were measured on the optical density of the color-forming reagent layer by reflection photometry using a visible ray having a central wavelength of 510 nm applied from the PET support side, without spotting a liquid sample and without subjecting to incubation. The measured optical density values for the fresh element ($F_D$) and the denatured elements ($F_D^*$) are set forth in Table 1.

TABLE 1

| Storage | None(Fresh) | 3 Months | 7 Months | 12 Months |
| --- | --- | --- | --- | --- |
| Optical Density | $F_D$ 0.227 | $F_D^*$ 0.255 | 0.284 | 0.310 |

10 μl of each of Samples 11–14 was deposited on the above-mentioned analytical element which was then incubated at 37° C. for 6 min. Immediately after the incubation was complete, optical density of the color-forming layer was measured by reflection photometry using a visible ray (central wavelength: 510 nm) which was applied from the PET support side.

The measured optical density values for the fresh element ($D_S$) and the denatured elements ($D_S^*$) are set forth in Table 2.

TABLE 2

| Storage | | Sample 11 | Sample 12 | Sample 13 | Sample 14 |
| --- | --- | --- | --- | --- | --- |
| None | $D_S$ | 0.259 | 0.522 | 0.821 | 1.154 |
| 3 Months | $D_S^*$ | 0.283 | 0.508 | 0.773 | 1.063 |
| 7 Months | | 0.305 | 0.516 | 0.763 | 1.004 |
| 12 Months | | 0.322 | 0.498 | 0.730 | 0.994 |

Figure 2:
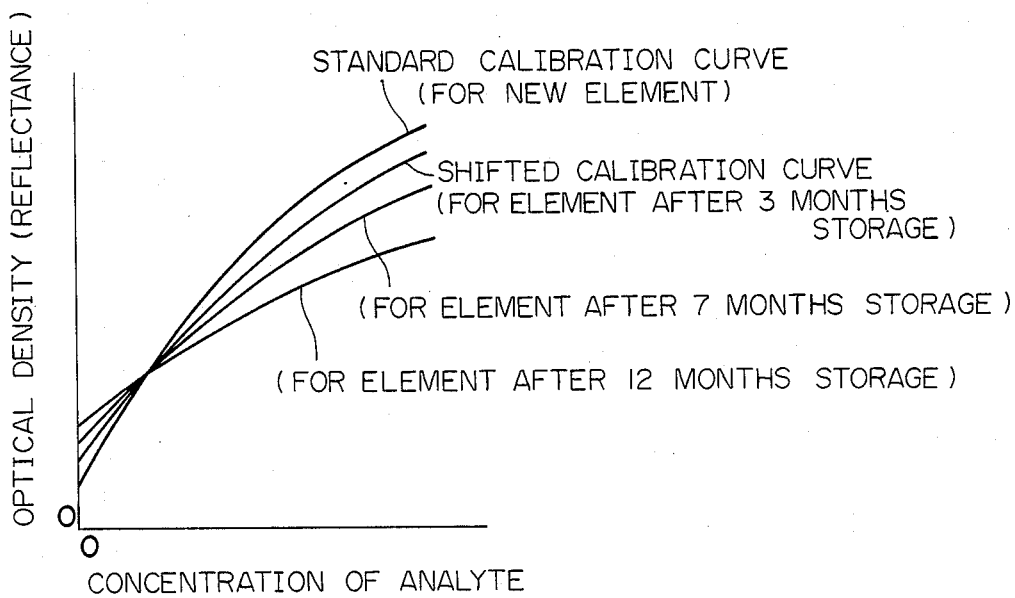
FIG. 2 schematically shows a standard calibration curve and three shifted calibration curves (due to forced denaturation of reagent in the analytical element) which are illustrated based on the optical density values by reflection photometry set forth in Example 1, Table 2 given hereinafter.

Accordingly, a calibration curve for the fresh slide for the glucose determination and calibration curves for the three slides denatured by storage take forms as illustrated schematically in FIG. 2.

Independently, an analytical slide was prepared in the manner as described in Reference Example 1 and denatured by keeping it under conditions of a surrounding temperature of 35° C. and a relative humidity of 30% for 5 months.

The above denatured slide and a freshly prepared analytical slide (which was prepared in the same manner as described in Reference Example 1, for the preparation of a standard calibration curve) were measured on the optical density of the color-forming reagent layer by reflection photometry using a visible ray having a central wavelength of 510 nm applies from the PET support side, without spotting a liquid sample and without subjecting to incubation. The measured optical density values for the fresh element ($F_D$) and the denatured element ($F_D^*$) are set forth in Table 3.

TABLE 3

| Storage | None (Fresh) | 5 Months |
| --- | --- | --- |
| Optical Density | $F_D$:0.227 | $F_D^*$:0.294 |

10 μl of each of Samples 15 and 16 was deposited on the above-mentioned analytical element which was then incubated at 37° C. for 6 min. Immediately after the incubation was complete, optical density of the color-forming layer was measured by reflection photometry using a visible ray (central wavelength: 510 nm) which was applied from the PET support side.

The measured optical density values for the fresh element ($D_S$) and the denatured element ($D_S^*$) are set forth in Table 4.

TABLE 4

| Storage | None (Fresh) | 5 Months |
| --- | --- | --- |
| Sample 15 | $D_S$:0.552 | $D_S^*$:0.533 |
| Sample 16 | $D_S$:0.941 | $D_S^*$:0.831 |

The values of the above $F_D$ and $F_D^*$ and the values of $D_S$ and $D_S^*$ for Samples 15 and 16 were introduced into the aforementioned equation (7) and the simultaneous equations were solved to obtain the constants "a" and "b". The results are given below:

$$a = -3.492$$

$$b = +1.644$$

The value "$D_S$" was calculated from the optical density value "$D_S^*$" given in Table 2 using the above values for "a" and "b" and the equation (7). The results are set forth in Table 5.

Independently, the optical density value given in Table 2 was converted into a glucose concentration using a standard calibration curve (Equation (1)) which had been prepared using the freshly prepared normal analytical slide of Reference Example 1. The results are set forth in Table 6. The optical density value given in Table 5 was also converted in the same manner to give a glucose concentration set forth in Table 7.

Table 5

| | ($D_S$) | | | |
|---|---|---|---|---|
| Storage | Sample 11 | Sample 12 | Sample 13 | Sample 14 |
| None (Fresh) | 0.259 | 0.522 | 0.821 | 1.154 |
| 3 Months | 0.263 | 0.512 | 0.817 | 1.127 |
| 7 Months | 0.264 | 0.527 | 0.836 | 1.137 |
| 12 Months | 0.261 | 0.509 | 0.836 | 1.137 |

TABLE 6

| | (unit: mg/dl) | | | |
|---|---|---|---|---|
| Storage | Sample 11 | Sample 12 | Sample 13 | Sample 14 |
| None (Fresh) | 0 | 90 | 229 | 493 |
| 3 Months | 9 | 85 | 208 | 392 |
| 7 Months | 17 | 88 | 197 | 344 |
| 12 Months | 23 | 82 | 180 | 302 |

TABLE 7

| | (unit: mg/dl) | | | |
|---|---|---|---|---|
| Storage | Sample 11 | Sample 12 | Sample 13 | Sample 14 |
| None (Fresh) | 0 | 90 | 229 | 493 |
| 3 Months | 0 | 86 | 227 | 459 |
| 7 Months | 0 | 91 | 237 | 471 |
| 12 Months | 0 | 85 | 237 | 471 |

Comparison of the concentration values set forth in Tables 7 and 6 clearly indicates that the denatured analytical slide gives precise glucose concentrations (which are almost identical to the concentration values obtained using a freshly prepared normal analytical slide) over a wide glucose concentration range.

EXAMPLE 2

The following seven liquid samples containing bilirubin of known amount were prepared. The bilirubin concentration was determined according to Jendrassik-Gróf diazo method.

Sample 21:
Monitrol IX
(Bilirubin concentration: 0.9 mg/dl)
Sample 22:
Monitrol IIX
(Bilirubin concentration: 4.5 mg/dl)
Sample 23:
Monitrol IX to which bilirubin was added and dissolved
(Bilirubin concentration: 8.4 mg/dl)
Sample 24:
Monitrol IX to which bilirubin was added and dissolved
(Bilirubin concentration: 13.0 mg/dl)
Sample 25:
Bilirubin Control (available from Americal Dade Corp.)
(Bilirubin concentration: 17.1 mg/dl)
Sample 26:
Human serum albumin     700 mg
Sodium chloride          90 mg
Bilirubin                0.1 mg
Add water to make        10 ml
(Bilirubin concentration: 1.0 mg/dl)
Sample 27:
Human serum albumin     700 mg
Sodium chloride          90 mg -continued Bilirubin                1 mg
Add water to make        10 ml
(Bilirubin concentration: 10.1 mg/dl)

A pluraltiy of analytical slides for quantitative analysis of total bilirubin in blood sample prepared and encased in plastic mounts in the manner as described in Example 1 of Japanese Patent Provisional Publication 61(1986)-71363 (hereinafter referred to as "bilirubin analytical slide") were divided into four groups, which were denatured by keeping them, respectively, under conditions of a surrounding temperature of 45° C. and a relative humidity of 30% for 4 days, 7 days, 10 days and 14 days.

The above denatured slides and a freshly prepared analytical slide (which was prepared in the same manner as described above, for the preparation of a standard calibration curve) were measured on the optical density of the color-forming reagent layer by reflection photometry using a visible ray having a central wavelength of 540 nm applied from the PET support side, without spotting a liquid sample and without subjecting to incubation. The measured optical density values for the fresh element ($F_D$) and the denatured elements ($F_D^*$) are set forth in Table 8.

10 μl of each of Samples 21–25 was deposited on the above-mentioned analytical slide which was then incubated at 37° C. for 6 min. Immediately after the incubation was complete, optical density of the color-forming layer was measured by reflection photometry using a visible ray (central wavelength: 540 nm) which was applied from the PET support side.

The measured optical density values for the fresh element ($D_S$) and the denatured elements ($D_S^*$) are set forth in Table 9.

TABLE 8

| Storage | None | D days | 7 days | 10 Days | 14 Days |
|---|---|---|---|---|---|
| Optical Density | $F_D$ 0.350 | $F_D^*$ 0.374 | 0.395 | 0.409 | 0.421 |

TABLE 9

| | ($D_S, D_S^*$) | | | | |
|---|---|---|---|---|---|
| | Sample No. | | | | |
| Storage | 21 | 22 | 23 | 24 | 25 |
| None (Fresh) | 0.447 | 0.624 | 0.760 | 0.881 | 0.967 |
| 4 Days | 0.473 | 0.644 | 0.775 | 0.892 | 0.975 |
| 7 Days | 0.487 | 0.659 | 0.787 | 0.906 | 0.981 |
| 10 Days | 0.494 | 0.662 | 0.794 | 0.914 | 0.989 |
| 14 Days | 0.508 | 0.675 | 0.798 | 0.915 | 0.999 |

Independently, a bilirubin analytical slide was prepared in the manner as described above and denatured by keeping it under conditions of a surrounding temperature of 45° C. and a relative humidity of 30% for 12 days.

The above denatured slide and a freshly prepared analytical slide (which was prepared in the same manner as above, for the preparation of a standard calibration curve) were measured on the optical density of the color-forming reagent layer by reflection photometry using a visible ray having a central wavelength of 540 nm applied from the PET support side, without spotting a liquid sample and without subjecting to incubation. The measured optical density values for the fresh element ($F_D$) and the denatured element ($F_D^*$) are set forth in Table 10.

TABLE 10

| Storage | None | 12 Days |
|---|---|---|
| Optical Density | $F_D$:0.350 | $F_D^*$:0.415 |

10 μl of each of Samples 26 & 27 was deposited on the above-mentioned analytical element which was then incubated at 37° C. for 6 min. Immediately after the incubation was complete, optical density of the color-forming layer was measured by reflection photometry using a visible ray (central wavelength: 540 nm) which was applied from the PET support side.

The measured optical density values for the fresh element ($D_S$) and the denatured element ($D_S^*$) are set forth in Table 11.

TABLE 11

| Storage | None (Fresh) | 12 Days |
|---|---|---|
| Sample 26 | $D_S$:0.455 | $D_S^*$:0.510 |
| Sample 27 | $D_S$:0.805 | $D_S^*$:0.839 |

The values of the above $F_D$ and $F_D^*$ and the values of $D_S$ and $D_S^*$ for Samples 26 and 27 were introduced into the aforementioned equation (7) and the simultaneous equations were solved to obtain the constants "a" and "b". The results are given below:

$$a = -0.923$$

$$b = +1.266$$

The value "$D_S$" was calculated from the optical density value "$D_S^*$" given in Table 9 using the above values for "a" and "b" and the equation (7). The results are set forth in Table 12.

TABLE 12

| | ($D_S$) | | | | |
|---|---|---|---|---|---|
| | Sample No. | | | | |
| Storage | 21 | 22 | 23 | 24 | 25 |
| None (Fresh) | 0.447 | 0.624 | 0.760 | 0.881 | 0.967 |
| 4 Days | 0.453 | 0.628 | 0.761 | 0.881 | 0.966 |
| 7 Days | 0.449 | 0.628 | 0.762 | 0.886 | 0.964 |
| 10 Days | 0.443 | 0.621 | 0.761 | 0.888 | 0.967 |
| 14 Days | 0.447 | 0.626 | 0.758 | 0.883 | 0.973 |

Independently, the optical density value given in Table 9 was converted into a bilirubin concentration using a standard calibration curve (Equation (1)) which had been prepared using the freshly prepared normal bilirubin analytical slide. The results are set forth in Table 13. The optical density value given in Table 12 was also converted in the same manner to give a bilirubin concentration set forth in Table 14.

TABLE 13

| | (unit:mg/dl) | | | | |
|---|---|---|---|---|---|
| | Sample No. | | | | |
| Storage | 21 | 22 | 23 | 24 | 25 |
| None (Fresh) | 0.9 | 4.5 | 8.4 | 13.1 | 17.1 |
| 4 Days | 1.0 | 5.0 | 8.9 | 13.6 | 17.5 |
| 7 Days | 1.4 | 5.4 | 9.3 | 14.2 | 17.8 |
| 10 Days | 1.6 | 5.5 | 9.6 | 14.6 | 18.3 |
| 14 Days | 2.0 | 5.8 | 9.7 | 14.6 | 18.8 |

TABLE 14

| | (unit:mg/dl) | | | | |
|---|---|---|---|---|---|
| | Sample No. | | | | |
| Storage | 21 | 22 | 23 | 24 | 25 |
| None(Fresh) | 0.9 | 4.5 | 8.4 | 13.1 | 17.1 |
| 4 Days | 1.0 | 4.6 | 8.4 | 13.1 | 17.1 |
| 7 Days | 0.9 | 4.6 | 8.5 | 13.3 | 17.0 |
| 10 Days | 0.8 | 4.4 | 8.4 | 13.4 | 17.1 |
| 14 Days | 0.9 | 4.5 | 8.3 | 13.1 | 17.4 |

Comparison of the concentration values set forth in Tables 13 and 14 clearly indicates that the denatured analytical slide gives precise bilirubin concentrations (which are almost identical to the concentration values obtained using a freshly prepared normal analytical slide) over a wide bilirubin concentration range.

We claim:

1. A method for correction of a calibration curve in a dry analytical process for quantitative analysis of an analyte in a liquid sample, wherein a standard calibration curve which has been previously determined for analysis of the analyte using a standard dry analytical element is corrected for application to a dry analytical element having deviated from the standard dry analytical element in its sensitivity to the analyte, utilizing an optical density determined on the deviated dry analytical element without the application of a liquid sample containing the analyte thereon.

2. The method for correction of a calibration curve as claimed in claim 1, wherein the standard calibration curve is corrected for application to the dry analytical element having deviated from the standard dry analytical element in its sensitivity to the analyte, utilizing an optical density determined on the deviated dry analytical element which has been subjected to incubation.

3. The method for correction of a calibration curve as claimed in claim 1, wherein the standard calibration curve is corrected for application to the dry analytical element having deviated from the standard dry analytical element in its sensitivity to the analyte, utilizing an optical density determined on the deviated dry analytical element which has received spotting of water or a liquid containing no analyte.

4. The method for correction of a calibration curve as claimed in claim 1, wherein the standard calibration curve is corrected for application to the dry analytical element having deviated from the standard dry analytical element in its sensitivity to the analyte, utilizing an optical density determined on the deviated dry analytical element which has received spotting or water or a liquid containing no analyte and then has been subjected to incubation.

* * * * *